United States Patent [19]

Scheps

[11] Patent Number: 5,506,616
[45] Date of Patent: Apr. 9, 1996

[54] DIFFERENTIAL IMAGING FOR SENSITIVE PATTERN RECOGNITION

[75] Inventor: Richard Scheps, Del Mar, Calif.

[73] Assignee: The United States of America as represented by the Secretary of the Navy, Washington, D.C.

[21] Appl. No.: 260,631

[22] Filed: Jun. 8, 1994

Related U.S. Application Data

[63] Continuation of Ser. No. 958,191, Oct. 7, 1992, abandoned.

[51] Int. Cl.⁶ .............................. H04N 7/00; H04N 7/18
[52] U.S. Cl. ............................................................ 348/31
[58] Field of Search .......................... 348/31, 162, 164, 348/28, 64; 382/2, 34; H04N 7/00, 7/18

[56] References Cited

U.S. PATENT DOCUMENTS

| | | |
|---|---|---|
| 3,663,813 | 5/1972 | Shaw . |
| 3,820,067 | 6/1974 | Shepard . |
| 4,047,023 | 9/1977 | Key et al. . |
| 4,200,861 | 4/1980 | Hubach et al. ............................ 382/34 |
| 4,259,009 | 3/1981 | Jernigan . |
| 4,584,704 | 4/1986 | Ferren ..................................... 358/227 |
| 4,731,663 | 3/1988 | Kovalchick et al. . |
| 4,751,706 | 6/1988 | Rohde et al. . |
| 4,862,257 | 8/1989 | Ulich ....................................... 358/98 |
| 4,917,500 | 4/1990 | Lugos . |
| 4,964,721 | 10/1990 | Ulich et al. .............................. 358/95 |
| 5,013,917 | 5/1991 | Ulich ....................................... 358/95 |
| 5,034,810 | 7/1991 | Keeler ..................................... 358/95 |
| 5,091,778 | 2/1992 | Keeler et al. ............................ 358/98 |
| 5,140,463 | 8/1992 | Yoo et al. ................................ 348/31 |
| 5,231,401 | 7/1993 | Kaman et al. ........................... 358/95 |
| 5,231,480 | 7/1993 | Ulich ....................................... 358/95 |
| 5,233,415 | 8/1993 | French et al. ........................... 358/95 |
| 5,257,085 | 10/1993 | Ulich et al. .............................. 356/73 |

OTHER PUBLICATIONS

Colorado Video Inc. Catalog, 1985/86 Short Form Catalog.
Article titled "Multiwavelength Lidar For Ozone Measurements In The Troposphere And The Lower Stratosphere" by Papayannis et al.
Colorado Video Inc., General Descriptions and Specifications.
Colorado Video, 1991 Short Form Catalog.
IT Imaging Technology in Research & Development dated May 1984, "Digital Photography", Glen Southworth.
"Object Recognizing Device" by Komatsu Seisakuso K. K.

Primary Examiner—Tommy P. Chin
Assistant Examiner—Vu Le
Attorney, Agent, or Firm—Harvey Fendelman; Thomas Glenn Keough; Eric James Whitesell

[57] ABSTRACT

A frequency agile laser illuminates a scene with floods of emissions of different wavelengths. As the wavelengths, or laser color changes, certain objects will stand out with respect to their background so that detection and recognition is enhanced to permit appropriate action. This technique has application in the location of underwater objects.

6 Claims, 2 Drawing Sheets

DIFFERENTIAL IMAGING FOR SENSITIVE PATTERN RECOGNITION

Statement of Government Interest

The invention described herein may be manufactured and used by or for the Government of the United States of America for governmental purposes without the payment of any royalties thereon or therefor.

This is a continuation of application Ser. No. 07/958,191, filed Oct. 7, 1992 now abandoned.

BACKGROUND OF THE INVENTION

A better way to locate and detect objects which blend into a background or are otherwise obscured has been and still is being sought. Optical systems have been used for detecting objects under water and have relied on the use of range gated conventional imaging. However, the optical systems are not entirely satisfactory since they tend to be incapable of detecting an object that blends into a background, such as, a light colored object on a light colored background, for example. An example of such a system is that disclosed in a published Japanese patent application #59-79285 that provides an object-recognizing device for distinguishing an object on a background that projects relatively broadband white light, not individual wavelengths, for a TV monitor having an innovative logic board to help distinguish an object from the background. Another imaging comparison system using white light is disclosed in the article entitled "Digital Photography" by Glen Southworth, *IT Imaging Technology in Research & Development*, May 1984. The imaging techniques in this article show a conventional use of the Colorado Video Inc. video-scan-converter-video-subtractor combination to display differences between sequential images illuminated in white light or some nonvarying illumination of sequential scenes. An evolution of atmospheric constituents is being monitored in the paper by A. Papayannis et al. entitled "Multiwavelength LIDAR for ozone measurements in the troposphere and the lower stratosphere", Applied Optics, vol. 29, no. 4, 1 Feb. 1990. Emitted radiation is used to perform a point-by-point monitoring of the ozone absorption due to the effects produced by aerosol and other interference gases.

Thus, there is a continuing need in the state of the art for a technique and system for distinguishing between an object and its background using a number of discrete narrow-band, frequency agile laser source emissions to enhance a backscatter contrast between a sought object and its background.

SUMMARY OF THE INVENTION

The present invention is directed to providing a method and apparatus for enabling the location of an object from its background by an enhanced backscatter contrast therebetween. A frequency agile laser source illuminates the object and background with sequential discrete wavelengths so that a detector provides representative spatially resolved image signals for an interconnected computer that provides spatially resolved images having an enhanced backscatter contrast due to the differences in spectral scattering by the object and background of the discrete wavelengths.

An object of the invention is to provide an improved method and apparatus for detecting an object against a background.

Another object is to provide an improved method and apparatus for detecting an object against a background relying on an illumination by discrete wavelengths of radiation.

Still another object is to provide an improved apparatus and method for detecting an object on a background in which a frequency agile laser emits at discrete sequential wavelengths to enable a detection of spectral scattering contrast between the object and the background.

Another object is to improve the image detection sensitivity by reason of the contrast between the object and its background which also serves to remove scattering noise from interfaces such as the ocean's surface.

Another object is to provide for an improved detection of an object irrespective of the type of detection used, such as black and white video or any suitable detection which has appropriate colored filters.

Another object is to provide for an improved detection of an object suspended near the surface in an attenuating medium by illuminating the medium with a wavelength that does not penetrate deeply into the medium.

These and other objects of the invention will become more readily apparent from the ensuing specification and drawings when taken in conjunction with the appended claims.

DESCRIPTION OF THE PREFERRED EMBODIMENT

The concept of differential imaging in accordance with this inventive concept is to a technique designed to improve the ability for the detection of camouflaged or poorly visible objects through contrast enhancement. By way of example, in general, the detection of a white object on a white background is difficult to detect either by the eye or by conventional imaging techniques. The differential imaging concept disclosed herein relies on the fact that, generally, different materials do not have identical spectral scattering curves over all wavelengths, even if they appear to be similar in color.

Figure 1:
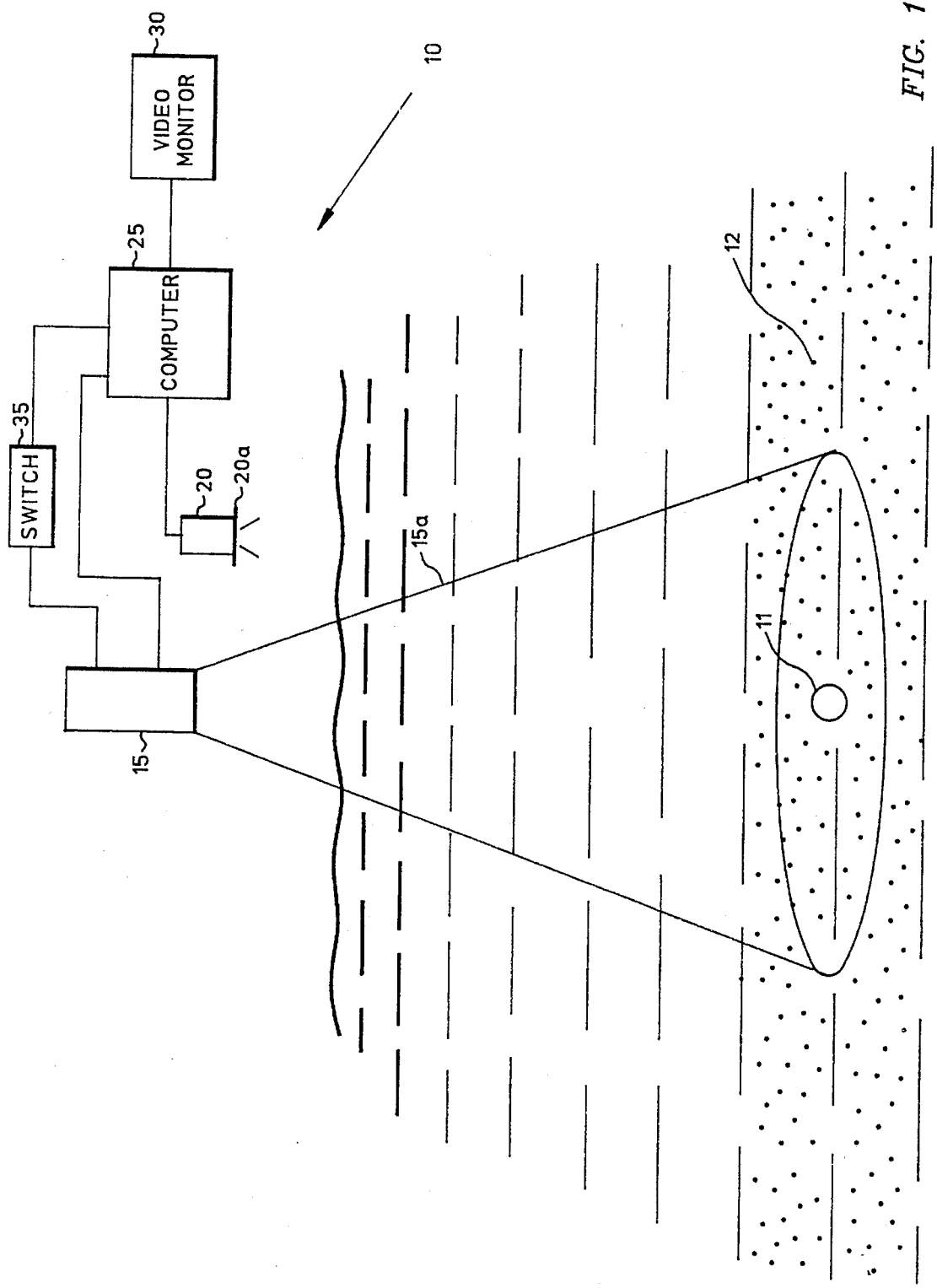
FIG. 1 depicts a schematic representative embodiment of the constituents of this inventive concept.

Referring now to FIG. 1 of the drawings a representative embodiment of a differential imaging pattern recognition system 10 is depicted operationally deployed as it seeks to locate an object 11 disposed above, at or on a similarly colored background such as the ocean floor 12 which could be sediment, sand or other typical ocean floor materials. An attempt to complicate the location of the object may have been done, such as, an intentional painting of the object so that it is more similar in appearance to the background, in this case, the ocean floor.

Figure 2A:
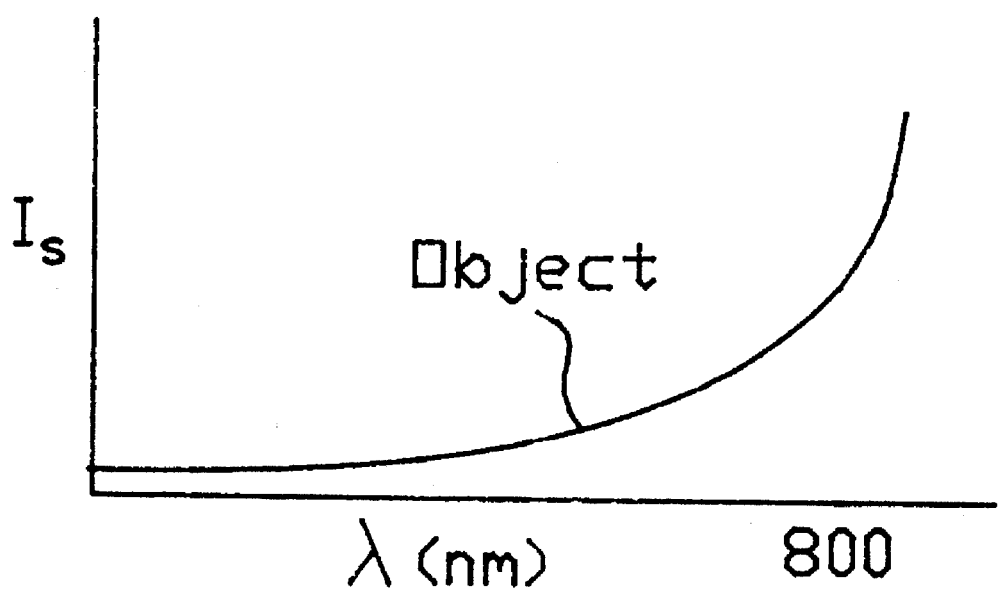
FIGS. 2a and 2b are schematic representations of hypothetical upward scattering curves for both the object and the background, in this case the ocean floor, when illuminated by discrete wavelengths of emission from a frequency agile laser.
Figure 2B:
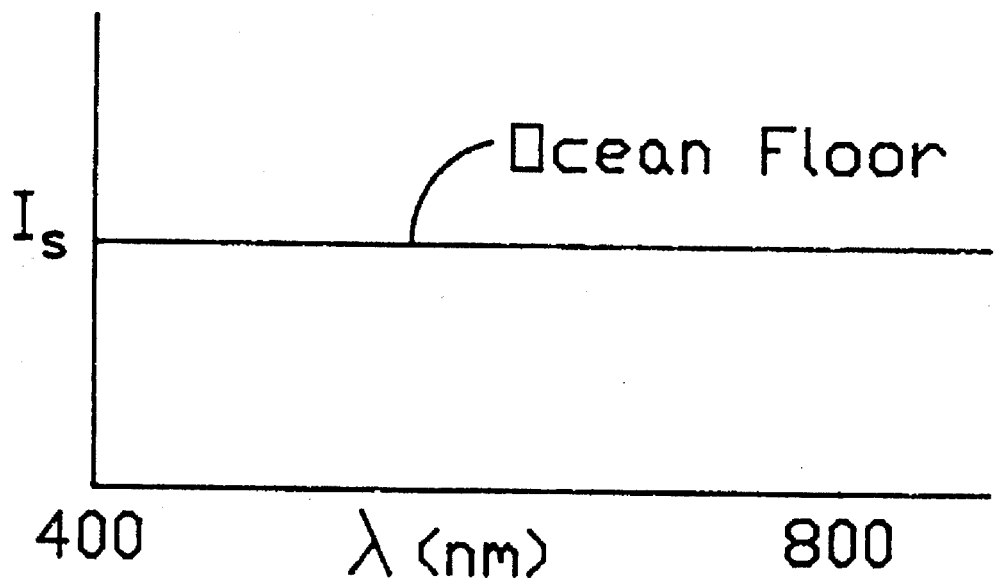

FIGS. 2a and 2b show two hypothetical upward scattering curves which are plots of scattering of impinging wavelengths versus wavelength. The upward scattered light is the light that is detected by the eye or a suitable detector. FIG. 2a shows that in the near IR, at around 800 nm, the object scatters much more light than the ocean floor which scatters more or less uniformly as depicted in FIG. 2b. These variations in scattering are due to inherent properties of the object and the background. For some applications this scattering variation near the IR may provide a sufficient enhancement of the contrast between the object and the background. However, in accordance with this inventive concept, if a series of at least two spatially resolved images are taken at different illuminating wavelengths; the different illuminating wavelength, spatially resolved images are digitized; and then the different illuminating wavelength spatially resolved images are compared, the details of the object to be detected become much enhanced.

The differential imaging in accordance with this inventive concept relies upon a tunable laser separately illuminating with two or more wavelengths. The spatially resolved images are compared (one way to compare them is by digitizing them and then subtracting them) with respect to successive wavelengths or between any two or among several other wavelengths. This improves the spatially resolved image contrast by, for example, allowing the subtracting out of the background (in this case, the ocean floor), leaving only the object in the image field.

A related benefit of this technology is that in the case shown, different wavelengths penetrate the transmissive medium (ocean, air) differently. A contrast enhancement can be improved by tuning the illuminating probe beam to wavelengths where the background is not particularly visible due to attenuation of the illuminating probe beam in its path through the medium. An sought object close to an illumination source would stand out while the background would appear dark because the illuminating wavelength is attenuated by the medium. However, if the object to be detected is further away, or as far away as the background (for example, something on the ocean floor), then the medium attenuation does not help in the location of the object.

Differential imaging pattern recognition system 10 includes an illuminator 15 that selectively and sequentially emits, scans discrete wavelengths of light that are within the range of between 180 nm and 10,000 nm in a "flooding" search beam 15a of illumination to cover an area in much the same manner as a floodlight covers an area. A tunable laser, multi-frequency laser or frequency agile laser with an appropriate lens arrangement, if needed, may be selected, such as, for example, a Ti:Sapphire laser as disclosed in the co-pending application of Richard Scheps, entitled "A Multifrequency, Rapidly Sequenced or Simultaneous Tunable Laser," Navy Case 73883, may be used. A number of commercially available Ti:Sapphire lasers with appropriate frequency doublers, triplers and associated frequency synthesizers could be chosen which are all freely available in the art to which this invention pertains. In addition, other frequency sources are available with the qualification that the sources be capable of discrete wavelength emissions in narrow bands. When the illumination is to be through seawater, discrete emissions in the blue-green spectrum may be more desirable to enable an illuminating and reflecting penetration through the water medium for the purposes of detection by means of enhanced scattering contrasts.

A detector 20 is proximately located with respect to the illuminator to receive a reflected spatially resolved image portion of the radiated emissions from illuminator 15. A commercially available black-and-white video camera providing analog, raster-scanned representative spatially resolved image signals might be used, for example, or a CCD array or a suitable still camera could be used having appropriate circuitry for generating the representative spatially resolved image signals. Appropriate filters 20a for filtering out certain light from other sources and non useful background light may or may not be included in association with the detector in accordance with established practices. Whichever recording means is selected for taking the spatially resolved image of the illuminated object-background scene, it must have a sufficient sensitivity and resolution which may include appropriate colored filters to receive the spatially resolved images created by the frequency agile laser emissions and create the representative spatially resolved image signals.

The analog representative spatially resolved image signals from detector 20 are coupled to a video-scan-converter-video-subtractor computer 25. The interconnected computer is suitably coupled to functionally provide a subtraction of one spatially resolved image from another that shows the differences between two or more sequential spatially resolved images for display on an interconnected video monitor 30. These differences in the spatially resolved images are largely attributed to the different levels of scattering which are created by one wavelength of illuminating emission from illuminator 15 or a different wavelength of illuminating emission from illuminator 15 as they are reflected and scattered from object 11 and background 12. Optionally, a different processing of the images other than subtraction could be chosen from those available in the state of the art, such as addition or a suitable logic enhancement technique to effect a comparison of images illuminated by the different wavelengths.

The video-scan-converter-video-subtractor computer is available in the state of the art and could be, for example, an interconnected Model 494 video scan converter to store and effect a high-speed analog/digital conversion while performing a scan format conversion and a Model 492 video subtractor to compare stored digitized images and provide difference video output signals. Both of these units of the video-scan-converter-video-subtractor computer are marketed by Colorado Video Inc. of Boulder, Colo. Other computer components could be selected in the art to effect a high-speed analog, digital and digital analog conversion that is capable of digitizing, storing and displaying the video information while performing a scan format conversion and to provide a dual memory video subtractor useful for single frame or real-time comparison of a reference image and images under analysis. The interconnected scan converter and video subtractor computer are suitably coupled to show the difference between two or more images for display on an interconnected video monitor in accordance with a technique known in the art, for example, see the above referred-to Digital Photography article by Glen Southworth that are to the display of sequential images illuminated of the same light source.

A switch 35 may be coupled to both illuminator 15 and computer 25 to synchronize the sequential illumination by flooded discrete wavelengths 15a from scanning frequency agile laser with the processing of the analog representative image signals in computer 25. Optionally, a separate switch may be dispensed with when the pulsing of the flooding illuminator 15 is controlled from computer 25, such as the internal digital video memory switching arrangement of FIG. 1 in the Southworth article. In either event, the sequences of images are produced by scattering and reflections from object 11 and background 12, when illuminated by the discrete wavelengths, to enable a comparison in computer 25 on a desired sequential basis.

For example, illuminator 15 is actuated by switch 35 to illuminate object 11 and background 12 area to be examined with a flood of a first illuminating wavelength 11. Switch 35 also enables scan-converter-video-subtractor computer 25 to gate in and receive the spatially resolved image received by detector 20 of the reflected and scattered portion of the wavelength $l_1$ illumination from object 11 and background 12. Next, the object and background are illuminated by a flood of a different wavelength $l_2$ emitted from illuminator 15 and scattering and reflections of $l_2$ from the object and background can be gated into scan-converter-video-subtractor computer 25. The spatially resolved images attributed to $l_1$ and $l_2$ are appropriately processed in computer 25 to generate signals representative of differences of the reflections and scattering between the reflected object and background attributed to the different illuminating wavelengths $l_1$ and $l_2$. The generated signals are fed to monitor 30 or other appropriate processing circuitry for display or appropriate utilization. More than two reflected wavelengths of emitted wavelengths $l_3$ through $l_n$ also can be suitably processed in accordance with this inventive concept until the right combination indicates most clearly what the object is and where it is located.

Operation of the device relies on a tunable laser which is tunable over a range as large as the visible spectrum although not necessarily continuously tunable therethrough. In the example given, the tunable laser of illuminator 15 illuminates a scene containing an object to be illuminated, a white plate, along with the background, on white sand. Since lighter shades or light colors may only appear the same in white light, generally speaking, at least one color at a discrete wavelength emitted from illuminator 15 is transmitted through the air or water and the plate may look or appear darker while the white sand background still appears lighter. It is not necessary to know the emitted laser color beforehand since the laser of illuminator 15 can illuminate the scene with a sequence of colors until one color or another makes the object appear to have a contrast from the background. As far as glare from the surface is concerned, the frequency agile source of illuminator 15 enables the subtracting out of the background glare levels before a search is made for the object or in the same manner as done in DIAL LIDAR. In other words, as the emitted laser emission changes, certain objects stand out, making them potentially easier to recognize. This is largely because of the different scattering coefficients associated with the background and an object of interest.

Obviously, many modifications and variations of the present invention are possible in the light of the above teachings. It is therefore to be understood that within the scope of the appended claims the invention may be practiced otherwise than as specifically described.

I claim:

1. An apparatus for generating a spatially resolved image of an object in a surrounding medium, comprising:

a radiation source for illuminating a background including said object, wherein said radiation source emits pulses of radiation, wherein said radiation comprises a separate wavelength band in each of said pulses, and whereto each said separate wavelength band has a corresponding attenuation with said surrounding medium for detecting said object against said background;

an image recorder for receiving a reflection signal from said object and said background for each of said pulses, and for generating a return signal representative of a spatially resolved image of said object and said background for each said reflection signal; and a processor operably coupled to said image recorder for subtracting at least one of said return signals from another of said return signals to form an object signal representative of said spatially resolved image of said object, whereto said background is substantially removed from said spatially resolved image of said object.

2. The apparatus of claim 1, further comprising a display operably coupled to said processor for displaying said object signal.

3. The apparatus of claim 1, wherein said radiation source is a frequency-agile laser.

4. The apparatus of claim 1, wherein at least one of said pulses comprises radiation having a wavelength that is substantially attenuated beyond a range of said object from said radiation source.

5. A method for generating a spatially resolved image of an object, comprising the steps of:

illuminating said object against a background with pulses of radiation, wherein said radiation comprises a separate wavelength band in each of said pulses, and wherein each said separate wavelength band has a corresponding attenuation within said surrounding medium;

receiving a reflection signal from said object and said background for each of said pulses;

forming a return signal representative of a spatially resolved image of said object and said background for each said reflection signal; and subtracting at least one of said return signals from another of said return signals to form an object signal representative of a spatially resolved image of said object, whereto said background is substantially removed from said spatially resolved image of said object.

6. The method of claim 5, further comprising the step of displaying said object signal.

* * * * *